United States Patent [19]
Wu

[11] Patent Number: 5,097,852
[45] Date of Patent: Mar. 24, 1992

[54] DENTAL SANITARY APPLIANCE

[76] Inventor: Tzung-I Wu, No. 416, Ta She Tzun, Hsin Shih Hsiang, Tainan Hsien, Taiwan

[21] Appl. No.: 756,548

[22] Filed: Sep. 9, 1991

[51] Int. Cl.⁵ .............................................. A45D 24/16
[52] U.S. Cl. .................................. 132/309; 132/323; 132/328
[58] Field of Search ............... 132/309, 311, 323, 324, 132/325, 326, 327, 328

[56] References Cited

U.S. PATENT DOCUMENTS

| | | | |
|---|---|---|---|
| 695,092 | 3/1902 | Cowan | 132/309 |
| 754,841 | 3/1904 | Bessonet | 132/325 |
| 1,220,409 | 3/1917 | Freschl | 132/309 |
| 1,656,823 | 1/1928 | Katz et al. | 132/309 |
| 1,695,238 | 12/1928 | Kalenoff | 132/309 |
| 1,738,389 | 12/1929 | Oliver | 132/309 |
| 2,047,456 | 7/1936 | Barsch | 132/325 |
| 2,601,244 | 6/1952 | Boulicault | 132/311 |
| 3,746,017 | 7/1973 | Casselman | 132/325 |
| 4,495,956 | 1/1985 | Fóurie | 132/326 |
| 4,655,233 | 4/1987 | Laughlin | 132/323 |

Primary Examiner—John J. Wilson
Attorney, Agent, or Firm—Morton J. Rosenberg; David I. Klein

[57] ABSTRACT

A dental sanitary appliance includes a toothbrush housing forming a frontal portion, a floss housing forming a middle portion of the dental sanitary appliance and a floss fastening member is insertable into the floss housing and incorporates a cover cap mountable on the rear end of the floss housing. The toothbrush housing has a toothbrush member and a chamber for accommodating a floss roll. The floss housing has a central passage in open communication with the chamber and a stopper attached to the upper wall of the rear portion of the central passage. The floss fastening member is movable in the central passage and includes a rod, a slit formed longitudinally on the top of the rod and a U-shaped frame member coupled to the rear end of the rod. The stopper can extend into the bottom of the slit when the rod is pushed longitudinally so as to terminate the outward movement of the rod. By this assembly, the toothbrush member of the toothbrush housing may be used to brush teeth and the floss having been firmly fixed by the stopper may be used to clean food remnants from between the teeth.

5 Claims, 3 Drawing Sheets

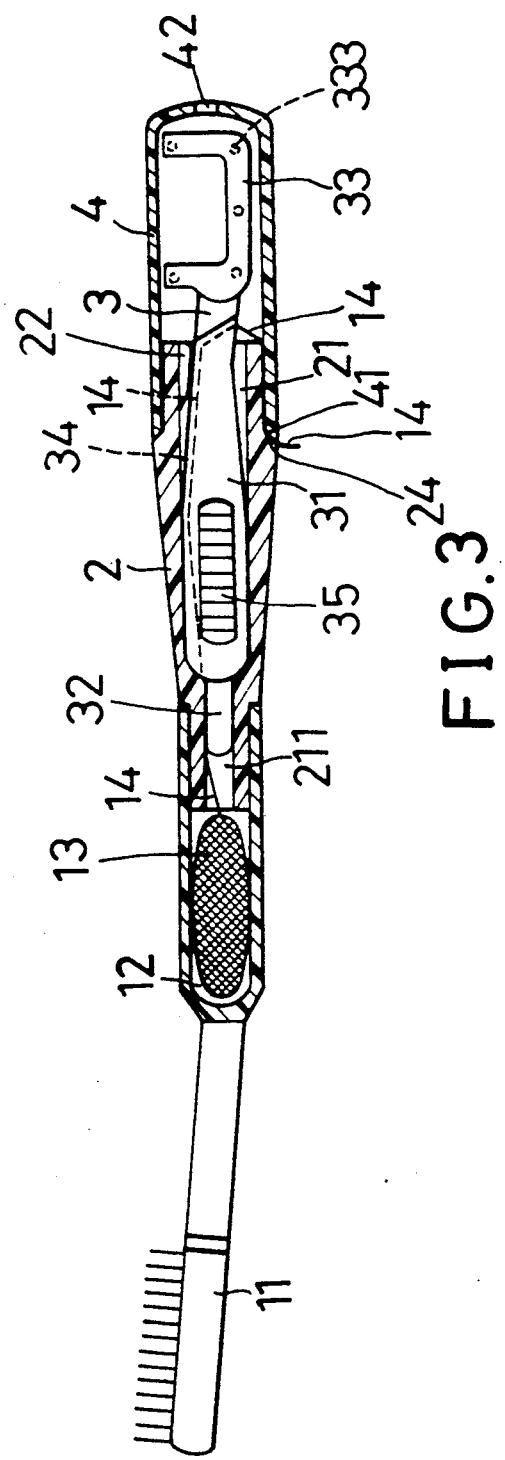
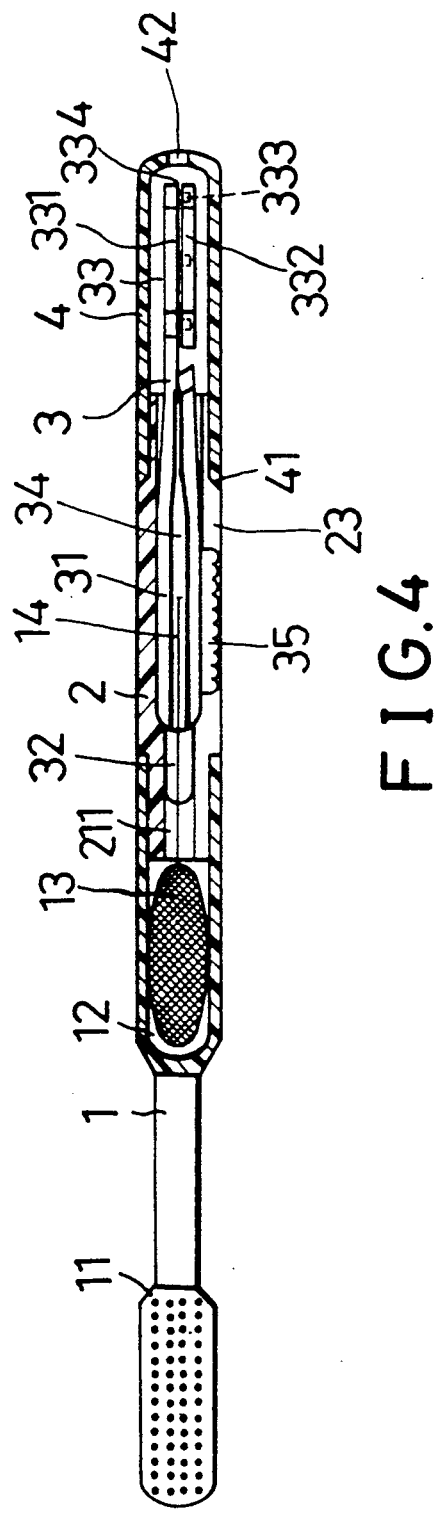
FIG.3
FIG.4

DENTAL SANITARY APPLIANCE

BACKGROUND OF THE INVENTION

1. Field of the Invention

This invention relates to a dental sanitary appliance having the functions of both a toothbrush and a flossing device.

2. Description of the Prior Art

Eating food is an enjoyable experience to most people. Essential to this experience is that the user have good teeth. Good teeth can help people to properly chew food for rapid digestion in the stomach. Generally speaking, people use a wide variety of toothbrushes to clean their teeth, however, food remnants between the teeth is difficult to clean by use of a toothbrush alone. Dental calculus formed on the teeth will cause a wide variety of periodontal diseases, such as odontorrhagia, gingivitis, dental caries and other types of dental diseases. People may have their teeth cleaned and washed by dentists one or two times a year. However, teeth washed by dentists may have the enamel coating destroyed and the teeth become more sensitive when they are stimulated by hot or cold foods. Therefore, a number of people also try to use floss to penetrate through the crevices of teeth and completely clean out food remnants.

SUMMARY OF THE INVENTION

It is the primary object of the present invention to provide a dental sanitary appliance including a toothbrush housing formed as a frontal portion of the appliance and a floss housing defining a middle portion as well a floss fastening member inserted into the floss housing and a cover cap mounted on a rear portion thereof. The toothbrush housing having a toothbrush member can provide the general function of brushing teeth. The floss fastening member with a U-shaped frame member is capable of fixing floss which is drawn from a floss roll stored in the toothbrush housing so as to provide the function of cleaning food remnants from the crevices of the teeth.

BRIEF DESCRIPTION OF THE DRAWINGS

FIG. 3 is a sectional elevational view showing the preferred embodiment of the subject invention;

FIG. 4 is a sectional plan view showing the preferred embodiment of the subject invention; and, FIG. 5 is an elevational sectional view showing a floss fastening member of the preferred embodiment of the subject invention in a drawn-out position.

DESCRIPTION OF THE PREFERRED EMBODIMENTS

Figure 1:
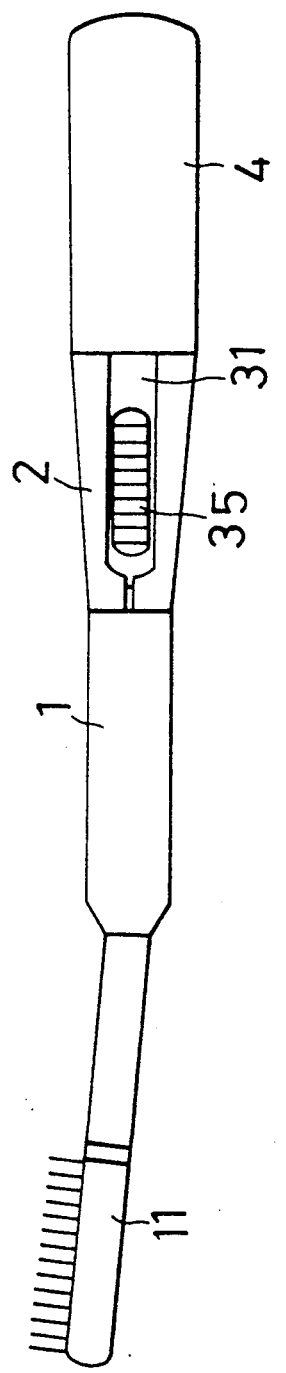
FIG. 1 is an elevational view of a preferred embodiment of the subject invention.
Figure 2:
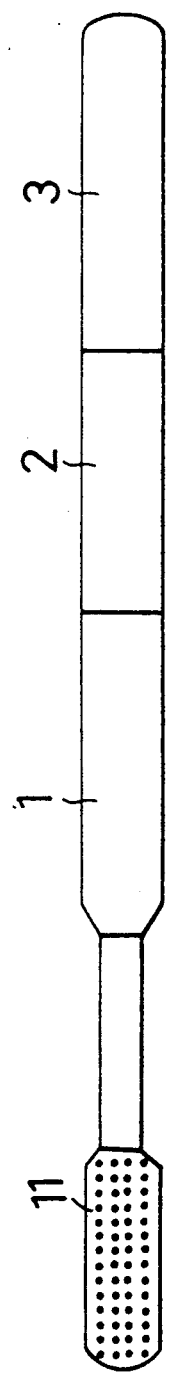
FIG. 2 is a plan view showing the appearance of the preferred embodiment of the subject invention.

As shown in FIGS. 1 and 2, the present invention is directed to a dental sanitary appliance including a toothbrush support housing 1 forming a frontal portion of the dental sanitary appliance, a floss housing 2 forming a middle portion thereof, a floss fastening member 3 being inserted into the floss housing 2 and a cover cap 4 being capable of being put on the rear portion of the floss housing 2.

The toothbrush support housing 1 has a toothbrush member 11 located at a front portion thereof and a chamber 12 formed in a rear portion. The chamber 12 is capable of accommodating a floss roll 13 as shown.

The floss housing 2 whose front end is inserted into the chamber 12 of the support housing 1 includes a central passage 21, a stopper 22, an elongate hole 23 and a circularly inclined face 24. The overall dental appliance extends in a longitudinal direction. A narrow passage 211 formed at the front portion of the central passage 21 is in open communication with the chamber 12 of the toothbrush support housing 1. The stopper 22 is attached to an upper wall of the rear portion of the central passage 21. The elongate hole 23 is opened on a side wall of the floss housing 2, as shown in FIG. 4. The circularly inclined face 24 is formed on one end of the elongate hole 23, as shown in FIGS. 3 and 5.

Figure 5:
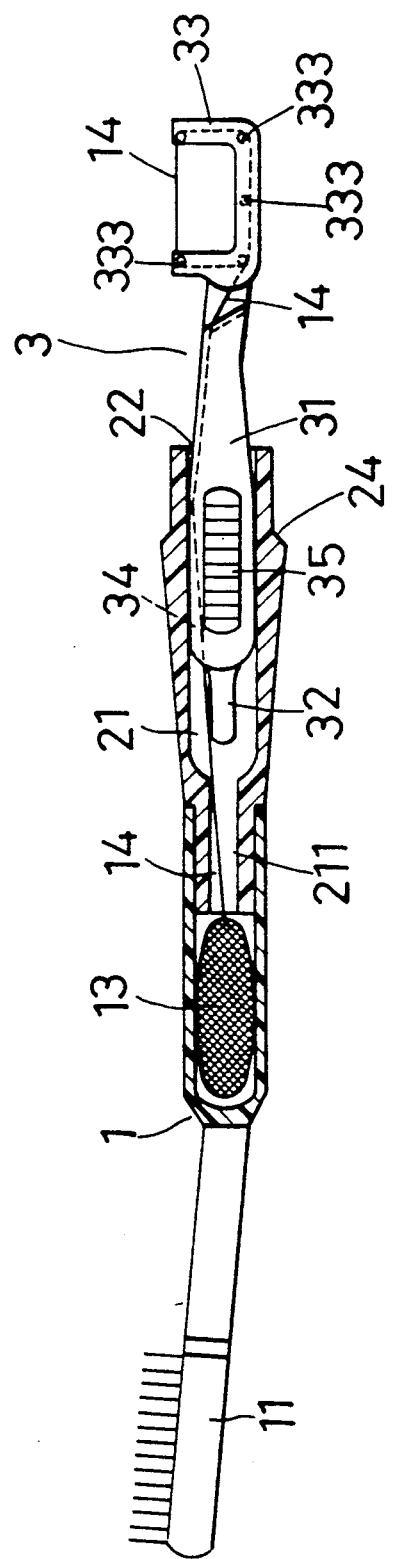

The floss fastening member 3 is movable or displaceable in the central passage 21 of the floss housing 2 extending in a longitudinal direction and includes a rod 31, a locating pin 32, a U-shaped frame member 33, a slit or trough 34 and a knob member 35 shown in FIGS. 3 and 5.

The frontal portion of the rod 31 is larger than the rear portion. The locating pin 32 disposed at the front end of the rod 31 is capable of being inserted into the narrow passage 211 of the central passage 21 of the floss housing 2. The U-shaped frame member 33 coupled to the rear end of the rod 31 is located external the central passage 21 of the floss housing 2. The U-shaped frame member 33 is formed by two U-shaped frames 331 and 332 which are coupled each to the other by a plurality of tongue in groove joints 333, as shown in FIGS. 3-5. A gap 334 formed between the two independent U-shaped frames 331 and 332 accommodates passage of floss 14 therebetween as shown in FIG. 4. The slit 34 disposed longitudinally on the top of the rod 31 is located below the stopper 22 of the floss housing 2. The width of the slit 34 is inclined from one end to the other so that floss 14 may easily pass through the slit 34. The knob member 35 is located on a side wall of the rod 31 corresponding to the elongated hole 23 of the floss housing 2 so that a user can contact the knob member 35 and move the rod longitudinally in an inward or outward direction.

The cover cap 4 includes a air hole 42 disposed within the center of its closed end and a circularly shaped and inclined face 41 formed on its open end. The circularly inclined face 41 mates in contiguous contact with circularly inclined face 24 of the floss housing 2. The air hole 42 provides ventilation and egress for moisture.

In operation, initially the toothbrush member 11 of the toothbrush housing 1 is used to brush teeth. The rod 31 as shown in FIG. 3, is insertable in the central passage of the floss housing 2. The locating pin 32 of rod 31 is insertable in the narrow passage 211 of the central passage 21 of the floss housing 2 so that the floss 14 which is drawn from the floss roll 13 is tightly held by the locating pin 32. Additionally, the floss 14 having passed through the slit 34 is capable of being fastened in the joint of the circularly inclined face 24 of the floss housing 2 and the circularly inclined face 41 of the cover cap 4. The floss 14 outside the joint of the circularly inclined face 24 and the circularly inclined face 41 allows the floss to be cut when the user rubs the floss 14 on the sharp edge of the inclined face 41.

When the floss 14 is used to clean food remnants from between the teeth, the user initially removes the cover cap 4 from the rear portion of the floss housing 2 and displaces the knob member 35 of the rod 31 longitudinally so as to move the floss fastening member 3 out of the central passage 21 of the floss housing 2, as shown in FIG. 5. At that time, the floss 14 is freed from being fixedly held by the locating pin 32 of the floss fastening member 3 and is capable of being drawn from the floss roll 13 as shown in FIG. 5. The rod 31 whose front portion is larger than the rear portion is moved outwardly until the stopper 22 of the floss housing 2 extends into the bottom of the slit 33 of the rod member 3 to fix the rod 31, and the floss 14 is tightly squeezed between the stopper 22 of the floss housing 2 and the slit 34 of the rod 31.

The gap 334 is narrow so that only the floss 14 can pass through. Moreover, the floss 14 is capable of being wound around the plurality of tongue in groove joints 333 of the gap 334 and is tightly fastened in the gap 334. As a result, the floss 14 is fixed between two ends of the opening of the U-shaped frame member 33 in a firm manner so that it is capable of being used to clean food remnants from teeth.

When the user is not operating the floss 14, he or she may displace the knob member 35 of the rod 31 longitudinally so as to move the rod 31 back to the central passage 21 of the floss housing 2. The cover cap 4 is placed on the rear portion of the floss housing 2 as shown in FIG. 3. If the used floss 14 is to be cut, the user may release the floss 14 from the U-shaped frame member 33, move the rod back to the central passage 21 of the floss housing 2 and place the cover cap 4 on the rear portion of the floss housing 2. The released floss 14 is squeezed in the joint of the circularly inclined face 24 of the floss housing 2 and the circularly inclined face 41 of the cover cap 4 when the user puts on the cover cap 4. The user may rub the released floss 14 which is external to the cover cap 4 on the sharp edge of the circularly inclined face 41 so as to cut the unnecessary released floss 14.

The dental sanitary appliance of the present invention is assembled by the toothbrush support housing 1, the floss housing 2, the floss fastening member 3 and the cover cap 4. Therefore, the dental sanitary appliance of the present invention is capable of being disassembled and replaced by new parts. For example, after having been used for an extended time, the toothbrush member 11 of the toothbrush housing 1 may be disassembled from the toothbrush housing 1 and may be replaced by a new one. Moreover, when the floss roll 13 stored in the rear portion of the toothbrush housing 1 is used up, there is the capability of having such replaced by a new one.

While the preferred embodiments of the invention have been described above, it will be recognized and understood that various modifications may be made therein and the appended claims are intended to cover all such modifications which may fall within the spirit and scope of the invention.

What is claimed is:

1. A dental sanitary appliance comprising:

a toothbrush support housing having a toothbrush member mounted on a frontal portion and a chamber formed in a rear portion, said chamber being capable of accommodating a floss roll;

a floss housing being insertable within said chamber of said toothbrush support housing and including a central passage formed therein, a stopper member, an elongated opening formed in a side wall thereof and a circularly inclined face, said central passage being in open communication with said chamber of said toothbrush housing, said stopper member being attached to an upper wall of the rear portion of said central passage, said circularly inclined face being formed on one end of said elongated opening; and, a floss fastening member being movable in said central passage of said floss housing and having a rod, a locating pin, a U-shaped frame member and a trough, said trough being disposed longitudinally on an upper surface of said rod and being capable of being passed through by a floss drawn from said floss roll of said toothbrush support housing, said floss being capable of being squeezed and fixedly secured by said stopper member of said floss housing when said floss fastening member is displaced longitudinally and is stopped by said stopper member extending into the bottom of said trough of said rod, said U-shaped frame member being coupled to the rear end of said rod and being external said floss housing, said U-shaped frame member being formed by two independent U-shaped frames wherein there is a narrow gap, said gap being capable of having floss wound thereupon, whereby said toothbrush member of said toothbrush support housing may be used to brush teeth and said floss having been respectively firmly fixed by said stopper member of said floss housing within said gap of said U-shaped frame member may be used to clean food remnants from said teeth of a user.

2. A dental sanitary appliance as defined in claim 1 wherein a cover cap is mounted on the rear portion of said floss housing and covers said U-shaped frame member of said floss fastening member, said cover cap having a circularly inclined face formed on an open end, said circularly inclined face corresponding to said circularly inclined face of said floss housing.

3. A dental sanitary appliance as defined in claim 1 wherein said cover cap has an air hole disposed on a closed end.

4. A dental sanitary appliance as defined in claim 1 wherein a narrow passage is formed at the front portion of said central passage of said supporting stand so that said locating pin of said floss fastening member is capable of being inserted and fixed therein.

5. A dental sanitary appliance as defined in claim 1 wherein a knob member is capable of being disposed on a side wall of said rod of said floss fastening member extending within said elongated hole of said and may be displaced by a user so as to move said rod of said floss fastening member longitudinally.

* * * * *